(12) United States Patent
Simonton

(10) Patent No.: US 8,377,136 B2
(45) Date of Patent: Feb. 19, 2013

(54) METHOD FOR STABILIZING AN INTERVERTEBRAL DISC DEVICE

(75) Inventor: Thomas Andrew Simonton, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 308 days.

(21) Appl. No.: 12/426,465

(22) Filed: Apr. 20, 2009

(65) Prior Publication Data
US 2010/0268155 A1    Oct. 21, 2010

(51) Int. Cl.
*A61F 2/44* (2006.01)
(52) U.S. Cl. ............... 623/17.16; 623/17.12; 623/17.11
(58) Field of Classification Search ..... 623/17.11–17.16
See application file for complete search history.

(56) References Cited

U.S. PATENT DOCUMENTS

| | | | |
|---|---|---|---|
| 4,618,490 A | 10/1986 | De Marco | |
| 6,132,759 A | 10/2000 | Schacht et al. | |
| 6,165,488 A | 12/2000 | Tardy et al. | |
| 6,287,588 B1 | 9/2001 | Shih et al. | |
| 6,863,899 B2 | 3/2005 | Koblish et al. | |
| 7,052,497 B2 | 5/2006 | Sherman et al. | |
| 2002/0151893 A1* | 10/2002 | Santilli | 606/61 |
| 2004/0230309 A1* | 11/2004 | DiMauro et al. | 623/17.12 |
| 2005/0042288 A1 | 2/2005 | Koblish et al. | |
| 2005/0203206 A1* | 9/2005 | Trieu | 523/113 |
| 2005/0261773 A1* | 11/2005 | Ferree | 623/17.16 |
| 2005/0267577 A1 | 12/2005 | Trieu | |
| 2006/0189986 A1 | 8/2006 | Sherman et al. | |
| 2006/0273279 A1* | 12/2006 | Kaplan et al. | 252/1 |
| 2007/0073397 A1* | 3/2007 | McKinley | 623/17.11 |
| 2007/0100453 A1* | 5/2007 | Parsons et al. | 623/17.14 |
| 2007/0213822 A1 | 9/2007 | Trieu | |
| 2007/0213823 A1 | 9/2007 | Trieu | |
| 2009/0162438 A1* | 6/2009 | Fuller et al. | 424/484 |
| 2010/0112029 A1* | 5/2010 | Scifert | 424/423 |

FOREIGN PATENT DOCUMENTS

EP    479582 A1 * 4/1992

OTHER PUBLICATIONS

Biotech article, "M-Biotech's Hydrogel Swelling Kinetics Monitoring System".
Article from Trends Biomater Artif. Organs, vol. 15 (1) pp. 4-6 (2001), "Preparation of Wound Dressing Using Hydrogel Polyurethane Foam" by Jae Suk Lee et al.
Article from Journal of Physics: Conference Series 3 (2004), pp. 22-28, "Polymer Chemistry and Hydrogel Systems", by EH Schacht.
Excerpt from National Textile Center Annual Report:Nov. 2003, pp. 1-10,"NTC Project M01-CR01 (formerly M01-B01)biodegradable Hydrogel-Textile Hybrid for Tissue Engineering".
Article from www.businesswire.com, Sep. 4, 2006, "Nanotherapeutics files Investigational New Drug application for NanoDOX Hydrogel to Treat Lower Extremity Diabetic Ulcers".

* cited by examiner

*Primary Examiner* — Eduardo C. Robert
*Assistant Examiner* — Nicholas Plionis

(57) ABSTRACT

The invention relates to a biocompatible settable polymer useful in retaining an implant, more evenly distributing any force loading on the implant, and/or promoting tissue growth around and onto the implant.

17 Claims, 3 Drawing Sheets

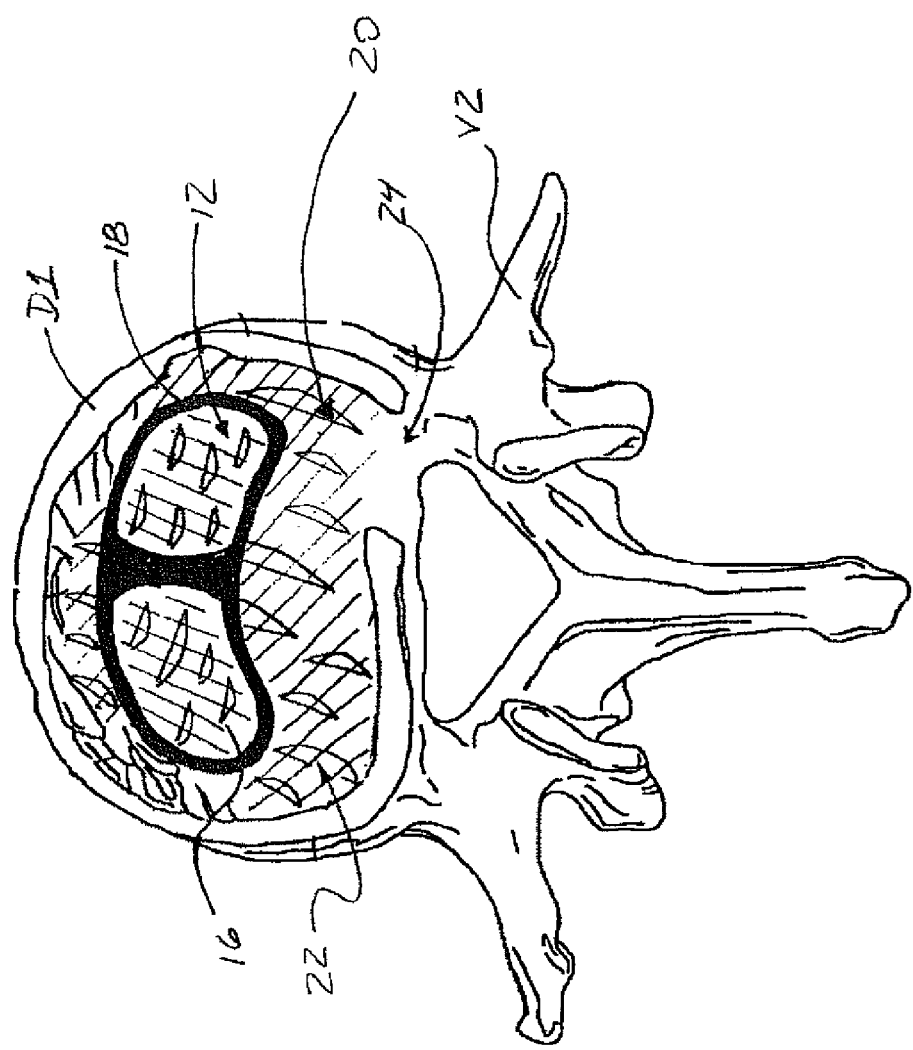

METHOD FOR STABILIZING AN INTERVERTEBRAL DISC DEVICE

The present invention relates to a settable polymer and methods of using the same.

BACKGROUND

The replacement or repair of damaged or diseased tissues by implantation is a continuing goal of the medical profession. However, there are a number of difficulties that restrict the use of implanted materials.

In particular, implantation of interbody devices into the intervertebral disc, which may be degraded or damaged by an external wound, disease, or aging, has received significant attention over the past decade. These interbody devices are typically synthetic vertebral body spacers that are inserted into the disc space after extraction of the affected intervertebral disc. However, these synthetic devices often fail to reproduce all of the mechanical properties inherent to the intervertebral disc, such as flexibility and load-buffering. In addition, the implant itself has the possibility of damaging the neighboring vertebrae and nerves. This is particularly true for interbody devices that may be dislodged from the disc under load conditions. Hence, it is quite important to prevent movement of the synthetic device after insertion into the patient.

Typically the synthetic interbody device is inserted by first making an opening in the anulus fibrosus and then inserting the interbody device through the opening. While, reduction in size of the opening and the insertion route, there is still an undesirably high chance for movement of the interbody device post implantation. In addition, many of the interbody devices on the market today have at least two bearing surfaces for engaging the two adjacent end plates, where the bearing surfaces often have engagement mechanisms that comprise studs, keels, and/or a porous surface.

A large number of interbody devices have been designed and produced, ranging from large cylindrical dowels to small rectangular wedges. Many of the interbody devices currently in use also have open passages through them (hollow spaces). Examples of interbody devices include, but are not limited to, the Adaptive Vertebral Spacer (AVS) AS, AVS TL, AVS AL, AVS PL, Vertebral Body Support System, and VLIFT Vertebral Body Replacement System, which are sold by Stryker, the DEVEX, LT & ST Mesh systems, and the Leopard, Jaguar and Saber cages, which are sold by DePuy, the BAK Vista interbody fusion system, which is sold by Zimmer Spine, and the INTER FIX™ and INTER FIX™ RP threaded fusion devices and the LT-CAGE® lumbar tapered fusion device, which are sold by Medtronic Sofamor Danek. See also, U.S. Pat. No. 6,923,810, and U.S. Pat. No. 6,758,849.

Because these interbody devices may be extruded, either partially or completely, from the site of implantation, there is a need in the market for a method of holding the device in place and/or filling void spaces between the device and the intended contact surfaces in the patient.

A particular class of polymers that have proven useful in biological applications are hydrogels, which consist of a three-dimensional network of hydrophilic polymers with water filling the space between the polymer chains. Hydrogels may be obtained by copolymerizing suitable hydrophilic monomers, by chain extension, and by cross-linking hydrophilic pre-polymers or polymers.

A thermoreversible hydrogel matrix, which is liquid near physiologic temperatures, has been shown to elicit vasculogenesis and modulate wound healing. This bioactive hydrogel material has also been shown to improve healing in response to implanted foreign materials; demonstrating a decrease in the surrounding fibrous capsule thickness and a persistent increase in blood supply immediately adjacent to implanted materials exposed to this thermoreversible hydrogel. However, that thermoreversible hydrogel is molten at physiologic temperatures, rendering it inappropriate for use in vivo (see WO 2003/072155).

U.S. Pat. No. 5,972,385 describes a matrix comprising a modified polysaccharide with collagen for tissue repair, which can be combined with growth factors.

U.S. Pat. No. 6,287,588 describes a matrix comprising a continuous biocompatible gel phase, such as a hydrogel, and a discontinuous particulate phase, such as microspheres, and a therapeutic agent contained in both phases. The '588 patent does not discuss any use in conjunction with an interbody device.

Additional publications and patents have described polymers and co-polymers for use in medical applications, such as drug delivery, tissue regeneration, wound healing, wound dressings, adhesion barriers, and wound adhesives. For example, see U.S. Pat. No. 4,618,490 and U.S. Pat. No. 6,165,488.

SUMMARY OF THE INVENTION

The invention relates to a settable hydrogel for retaining an implant, more evenly distributing any force loading on the implant, and/or promoting tissue growth around, through and/or onto the implant. Optionally, the hydrogel may have a pore creating material, that may optionally carry a therapeutic agent.

The invention relates to injection of an in situ curing polymer around and/or through a porous interbody device, wherein the cured polymer at least partially fills a void or space around the interbody device, at least partially fills a hollow space within the interbody device, at least partially fills a fissure in the disc annulus, aids in distributing a load across the disc space, e.g., dissipates point loading, and/or at least partially interlocks the interbody device with surrounding tissue to reduce the risk of expulsion back out through the insertion site.

In an exemplary embodiment, the polymer is a hydrophilic polymer comprising poly vinyl alcohol (PVA) and copolymers thereof. In another exemplary embodiment, the polymer is cross-linked using free radical polymerization that is redox initiated.

The invention also provides a method of improving retention of an interbody device within a subject where an interbody device is inserted through an opening in the annulus of a subject and a biologically compatible polymer and a cross-linking agent are injected into the opening of the annulus where the biologically compatible polymer cures to seal the opening and retain the interbody device within the subject. Optionally the biologically compatible polymer may comprise a bioabsorbable pore creating material and/or a therapeutic agent. Therapeutic agents include, but are not limited to, analgesics, anti-microbial agents, bone growth agents and combinations thereof.

In another exemplary embodiment, the invention provides a method of improving the dynamic stability of an interbody device, where an interbody device having at least two articulating members is inserted into a subject and a biologically compatible polymer and a cross-linking agent are injected between the two articulating members of the interbody device, where it cures to form a resilient structure between the two articulating members of the interbody device and improves the dynamic stability of the implant. Optionally the biologically compatible polymer may comprise a bioabsorbable pore creating material and/or a therapeutic agent. Therapeutic agents include, but are not limited to, analgesics, anti-microbial agents, bone growth agents and combinations thereof.

In yet another exemplary embodiment, the invention provides a method of improving retention of an interbody device within a subject where an interbody device has at least one hollow space, opening or indentation and the biologically compatible polymer and a cross-linking agent are injected into the at least one hollow space, opening or indentation of the interbody device where it cures and improves retention (reduces extrusion) of the interbody device within the subject. Optionally the biologically compatible polymer may comprise a bioabsorbable pore creating material and/or a therapeutic agent. Therapeutic agents include, but are not limited to, analgesics, anti-microbial agents, bone growth agents and combinations thereof.

The invention also relates to the manufacture of a medicament for application in conjunction with insertion of an interbody device and a kit comprising an in situ settable polymer and an interbody device.

BRIEF DESCRIPTION OF THE DRAWINGS

FIG. 2 is a top plan view of a vertebra with a single implant device positioned in the disc space.

DETAILED DESCRIPTION OF THE INVENTION

Figure 1:
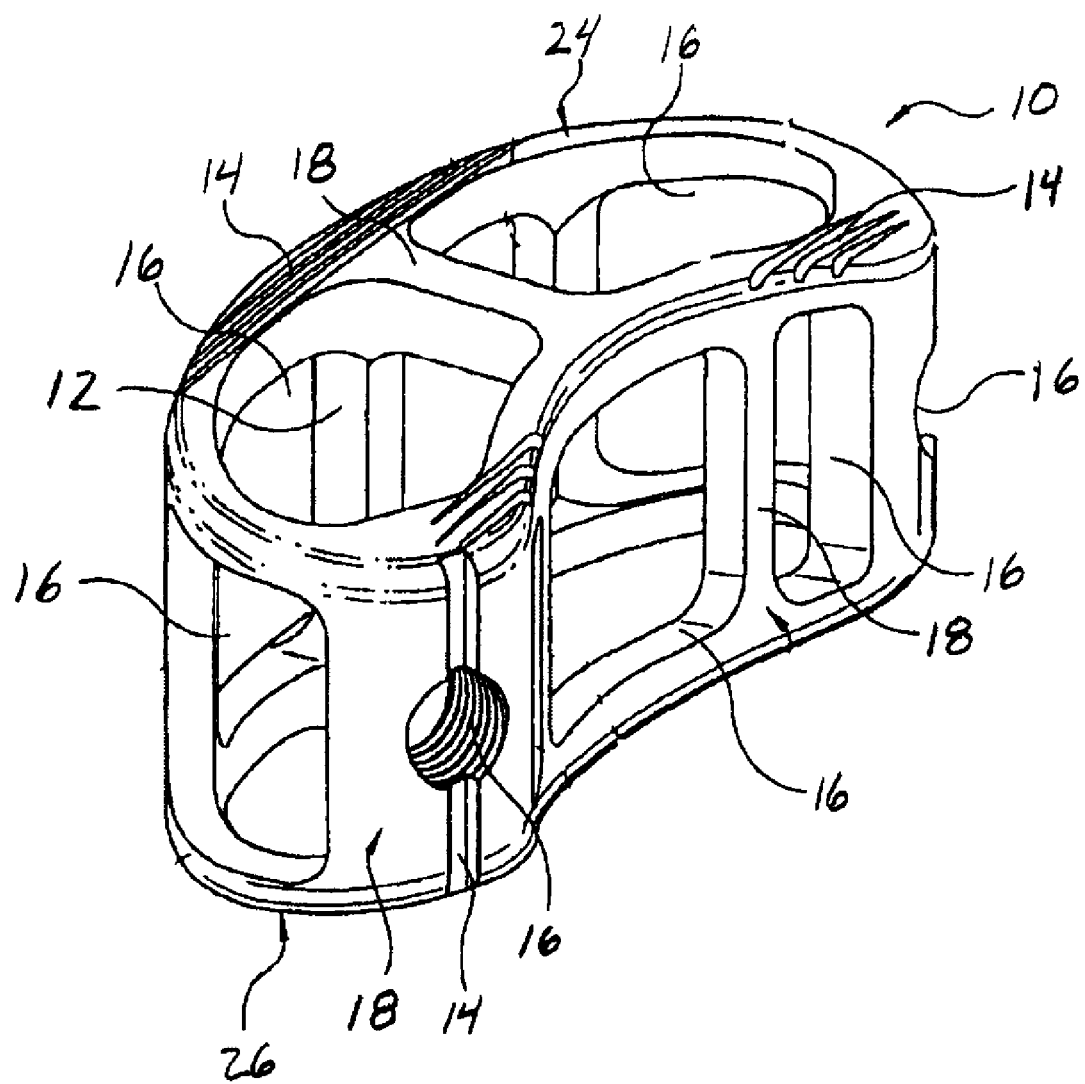
FIG. 1 is a perspective view of an implant device having multiple grooves or indentations, openings and a hollow interior space.

For the purposes of promoting an understanding of the principles of the invention, reference will now be made to certain embodiments and specific language will be used to describe the same. Nevertheless, it will be understood that no limitation of the scope of the invention is intended by the reference to the embodiments and that alterations and further modifications of the illustrated device, along with further applications of the principles of the invention described herein, will be recognized in light of the present disclosure by one skilled in the art to which the invention relates.

The uses of the terms "a" and "an" and "the" and similar references in the context of describing the invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, each separate value in the range is incorporated into the specification as if it were individually recited herein.

All methods described herein may be performed in any suitable order unless otherwise indicated or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element is essential to the practice of the invention.

As used herein, "comprising," "including," "containing," "characterized by," and grammatical equivalents thereof are inclusive or open-ended terms that do not exclude additional, unrecited elements or method steps, but will also be understood to include the more restrictive terms "consisting of" and "consisting essentially of."

As used herein, "subject" means any mammal, including a human.

The spine is composed of a column of vertebrae that are individually separated from each other by intervertebral discs. The spinal cord runs through the length of the spine and the discs act like shock absorbers and stabilizers between adjacent vertebrae. As a result, the discs must be able to absorb mechanical loads while simultaneously permitting constrained flexing of the spine. As people age the discs can begin to breakdown or suffer injury, which frequently results in an abnormal reduction in disc height. This will frequently lead to severe back pain, which may be corrected by the removal of some or all of the disc material and insertion of an interbody device or interbody spacer between the two adjacent vertebrae to restore the proper spacing between the adjoining vertebrae and relieve pressure on nearby nerves.

There are a number of intervertebral devices that may be inserted into a defective disc to try and reduce the pain associated with the collapse of the disc. However, many of these devices suffer from the short coming of the device being extruded in response to force loading and/or motion. The present invention overcomes this limitation by using an in situ curing polymer that can be extruded around and/or into the device. When the cured polymer occupies spaces around or within the interbody device and provides a continuous contact between the surrounding tissue and the device it will secure the interbody device in place and prevent or reduce the tendency of the devise to be extruded. It will also help spread loading forces and when used with a pore creating material it may also facilitate bone growth and fusion. For example, a pore creating material may include BMP-2 to help induce bone growth and colonization of the pores. Thus the present invention provides an in situ settable polymer to help hold an interbody device in place and to help spread the force from one vertebra through the interbody device and on to the next vertebra. In exemplary embodiments the in situ settable polymer may include a pore creating material and/or therapeutic agent, which may be beneficially utilized to increase bone and/or soft tissue growth in and/or around the interbody device.

While the use of an in situ curing polymer to secure the interbody device in the patient does not require the presence of a pore creating material and/or a therapeutic agent, these agents may be beneficial where fusion of the adjacent vertebral bodies is desired. Thus, an exemplary embodiment of the invention involves the use of an in situ curing polymer in combination with a pore creating material therein, where the pore creating material may optionally comprise a therapeutic agent. In these embodiments, the pore creating material and in situ curing polymer are preferably absorbed or degraded with the rate of absorption or degradation being faster for the pore creating material than the in situ curing polymer, such that pores are created in the in situ curing polymer as the pore creating material is absorbed or degraded. For example, the pore creating material may include a therapeutic agent, such as a bone growth inducing agent, such as BMP-2, BMP-7, BMP-12 and/or GDF-5, that is released as the pore creating material is being gradually absorbed and/or degraded, thereby assisting in the recruitment of desirable cell lineages to the pore sites.

U.S. Pat. No. 7,361,193, issued Apr. 22, 2008, describes an exemplary interbody spacer where fusion of the adjacent vertebral bodies around the interbody spacer is desirable. As illustrated in FIGS. 1 and 2, such an interbody device 10 may have a hollow interior 12, an indentation or groove 14 on the device 10, and/or an opening 16 through an outer wall 18 of the device 10. Either prior to, during or following insertion of the interbody device 10 within a vertebral disc D1 an in situ curing polymer 20 may be injected into and/or around the device. For example, a settable biodegradable polymer may be injected through an opening 16 in an outer wall 18 of the device 10 to fill the hollow interior 12 and any space 22 surrounding the device 10. In this situation, it may be desirable to utilize a pore creating material and/or a therapeutic agent, for example, BMP-2, BMP-7, BMP-12, GDF-5 and/or another bone growth inducing agent. In this embodiment the biodegradable polymer provides initial dynamic stability to the implant device 10, helps to more evenly distribute compression forces by filling the openings 16 in the outer walls, such as those in contact with an adjacent vertebra, and in those exemplary embodiments utilizing a pore creating material, as that material is absorbed or degraded the resulting pores promote cellular colonization of the polymer by osteoblasts and other cells that are useful for bone growth. For example, where the top 24 and bottom 26 of the device 10 are going to be in contact with the adjacent vertebra V2 the polymer may flow around and/or through the device 10 so as to fill any spaces between the device 10 and the adjacent disc and vertebra tissues.

In another exemplary embodiment, the settable biocompatible polymer adheres to the surrounding vertebral bodies with sufficient force, and has sufficient elasticity and/or tensile strength, to help retain the implant device 10 within the disc space and prevent extrusion of the device 10 out through the implant opening 24. For example, the biocompatible polymer may have a modulus of elasticity in the set condition sufficient to withstand between about 1 to about 6 Megapascals of intradiscal pressure.

Other exemplary implant devices 10 include, but are not limited to those disclosed in U.S. Pat. No. 7,125,425, issued Oct. 24, 2006, U.S. Pat. No. 7,326,251, issued Feb. 5, 2008, U.S. Pat. No. 6,371,988, issued Apr. 16, 2002, U.S. Pat. No. 5,860,973, issued Jan. 19, 1999.

Figure 3A:
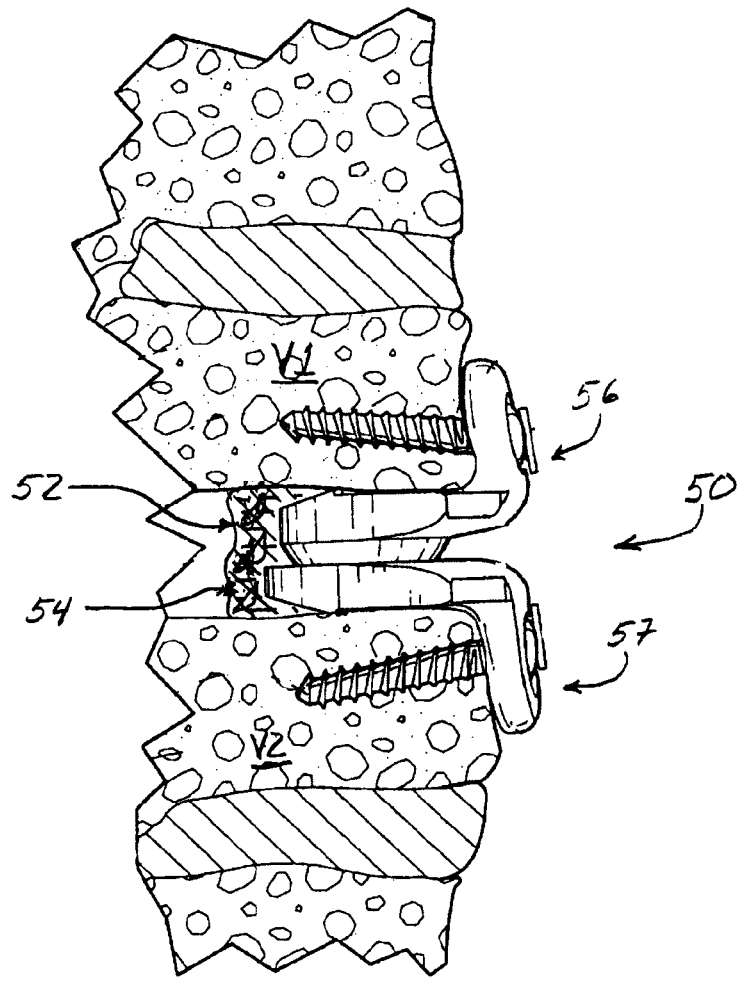
FIG. 3B is a cross-sectional view of an articulating implant device.
Figure 3B:
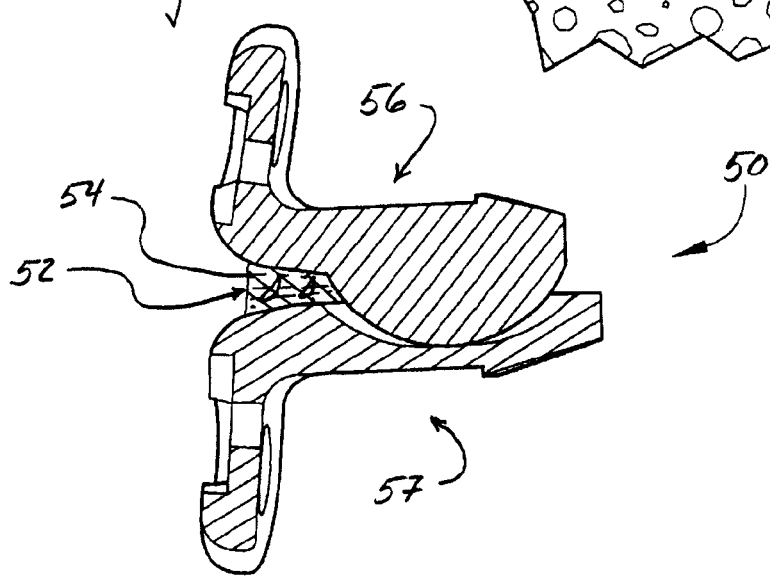

U.S. Pat. No. 6,113,637, issued Sep. 5, 2000, describes an exemplary articulating interbody spacer 50, (illustrated in FIG. 3) where bone growth between the adjacent vertebral bodies may be undesirable, but were dynamic stability of the device may be improved by filling desirable areas 52 (an indentation) between surfaces of the implant device 50 and around the implant device 50 (which includes an indentation) with an in situ curing polymer 54. In an exemplary embodiment, a biocompatible, non-absorbable, quick setting polymer 54 is injected into the space 52 between the adjacent vertebrae V1, V2 and in contact with the device 50 (FIG. 3a) and/or between two articulating members 56, 57 (FIG. 3b) of the device 50. In an exemplary embodiment, the polymer is a high viscosity polymer that cures to form a resilient structure around and/or near the implant device 50 to improve the dynamic stability of the device 50.

The "polymer" of the invention means a biologically compatible polymer that, when applied in combination with a cross-linking agent, sets to provide a resilient polymer.

The polymer preferably possess such qualities as mechanical strength, promotion of tissue formation, biodegradability, biocompatibility, sterilizability, optimum curing temperature, tensile strength, adhesion and/or good bonding strength. In an exemplary embodiment, the polymer, for example, a biologically absorbable hydrophilic polymer, cures, or partially cures, very rapidly upon delivery. Preparation of in-situ curable materials is known in the art and is disclosed, for example, in U.S. Pat. Nos. 6,703,041, 6,287,588, 6,312,725, 7,070,809 and 7,135,140.

A wide variety of biocompatible polymeric materials may be used, including, but are not limited to, silicon, polyurethane, copolymers of silicon and polyurethane, polyolefins, such as polyisobutylene and polyisoprene, neoprene, nitrile, polyvinyl alcohol, acrylamides such as polyacrylic acid and poly(acrylonitrile-acrylic acid), non-biologically absorbable polyurethanes, polyethylene glycol, poly(N-vinyl-2-pyrrolidone), acrylates such as polyacrylates, poly(2-hydroxy ethyl methacrylate), methyl methacrylate, 2-hydroxyethyl methacrylate, and copolymers of acrylates with N-vinyl pyrrolidone, N-vinyl lactams, acrylamide, polyurethanes and polyacrylonitrile, glycosaminoglycans, polyethylene oxide, co-polymers of PVA and PVP, and combinations thereof. The hydrogel materials may further be cross-linked to provide further strength. Examples of polyurethanes include thermoplastic polyurethanes, aliphatic polyurethanes, segmented polyurethanes, hydrophilic polyurethanes, polyether-urethane, polycarbonate-urethane and silicon polyether-urethane. Other suitable hydrophilic polymers include naturally-occurring materials such as glucomannan gel, polyphosphazenes, hyaluronic acid, polysaccharides, such as cross-linked carboxyl-containing polysaccharides, alkyl celluloses, hydroxyalkyl methyl celluloses, sodium chondroitin sulfate, cyclodextrin, polydextrose, dextran, gelatin, and combinations thereof.

Other suitable examples of biologically acceptable polymers include biocompatible homopolymers and copolymers of hydrophilic monomers such as 2-hydroxyalkyl acrylates and methacrylates, N-vinyl monomers, and ethylenically unsaturated acids and bases; polycyanoacrylate, polyethylene oxide-polypropylene glycol block copolymers, polygalacturonic acid, polyvinyl pyrrolidone, polyvinyl acetate, polyalkylene glycols, polyethylene oxide, collagen, sulfonated polymers, vinyl ether monomers or polymers, alginate, polyvinyl amines, polyvinyl pyridine, and polyvinyl imidazole. One can also use superabsorbent polymers (SAP) with or without additives. Superabsorbent polymers may include polymer chains that are synthetic, natural, and hybrid synthetic/natural polymers. Exemplary superabsorbent polymers may include, but are not limited to, polyacrylic acid, polymethacrylic acid, polymaleic acid, copolymers thereof, and alkali metal and ammonium salts thereof; graft copolymers of starch and acrylic acid, starch and saponified acrylonitrile, starch and saponified ethyl acrylate, and acrylate-vinyl acetate copolymers saponified; polyvinylpyrrolidone, polyvinyl alkylether, polyethylene oxide, polyacrylamide, and copolymers thereof; copolymers of maleic anhydride and alkyl vinylethers; saponified starch graft copolymers of acrylonitrile, acrylate esters, vinyl acetate, and starch graft copolymers of acrylic acid, methyacrylic acid, and maleic acid; the product of crosslinking acrylamide with backbones of kappa-carrageenan and sodium alginate using methylenebisacrylamide and potassium persulfate; and the product of crosslinking, using a bifunctional crosslinking reagent, an acyl-modified protein matrix such as soy protein isolate which has been acyl-modified by treatment with ethylenediaminetetraacetic acid dianhydride; mixtures and combinations thereof. Further, one can use silicon-based materials, polyethylene terephthalate, polycarbonate, thermoplastic elastomers and copolymers such as ether-ketone polymers such as poly etheretherketone.

The term "pore creating material" means a substance that is dispersed within the polymer prior to delivery into a patient and that creates a porous structure when removed (e.g., absorbed or degraded) from the polymer. Pore creating materials are preferably used with biodegradable polymers. The initial ratio of the polymer to the pore creating material may be between about 5% and about 95%, between about 15% and about 85%, or between about 25% and about 75%, wherein removal of the pore creating material from the biologically absorbable or degradable polymer creates pores of between about 100 μm and about 400 μm or between about 250 μm and about 350 μm.

In those embodiments were the polymer is intended to be absorbed or degraded in the patient, it may be absorbed or degraded over about a year, about 3 to about 9 months, about 3 to about 6 months, or about 6 to about 9 months.

In the context of this application, the pore creating material may be removed from the polymer in vivo, after the composition is applied to the patient. The term "removed" means a gradual removal by resorbtion, resorption, dissolution, bursting, disintegration, degradation and so forth. Optionally the pore creating material and/or polymer releases a therapeutic agent.

In some embodiments, the pore creating material may comprise microparticles or nanoparticles, such as spheres, rods, pellets, beads, and so forth, made from biologically absorbable materials. In preferred embodiments, the pore creating material is provided as microspheres with a diameter between about 50 microns to 400 microns, between about 100 microns and about 300 microns, or between about 100 microns and about 200 microns.

If the polymer is the same chemical structure as the pore creating material, the pore creating material is formulated such that the rate of removal of the pore creating material from the polymer is faster than the rate that the polymer is removed from the patient's body. For example, the polymer may be modified, such as by cross-linking, to ensure that its stays in the body for longer period of time, in which case the pore creating material would not be cross-linked or would have less cross-linking such that it is removed faster. For example, a pore creating material may be a microparticle made of a hydrogel, fast resorbing cements or ceramics, hyaluronic acid, collagen, sugars or polysaccharides, and so forth.

Microparticles or nanoparticles, with or without a therapeutic agent, may be prepared by any techniques known and used in the art. Such techniques include, but are not limited to, single and double emulsion solvent evaporation, spray drying, solvent removal, phase separation, simple and complex coacervation, and interfacial polymerization. Suitable techniques for preparing microparticles or nanoparticles, with a therapeutic agent are disclosed, for example, in Remington: The Science and Practice of Pharmacy, 21st edition, Lippincott Williams & Wilkins (2005) and U.S. Pat. Nos. 6,479,065, 6,998,074, 7,381,716, and 7,332,351.

By way of a non limiting example, microspheres may be produced by extrusion-spheroidization, where the active therapeutic ingredient and any inactive ingredients (excipients, binders, etc.) are pre-mixed, then wetted with water, in a high shear mixer to form a damp mass. The damp mass is then transferred into an extruder where it is forced through a screen or die plate, where it forms an essentially solid, extrudate of substantially uniform shape and size. The shaped extrudate may then be fed onto a rotating disk, which may be smooth or may contain a grid (waffled, grooved, etc.) where the shaped extrudate is broken into smaller pieces, which in time may be worn into a rounded or substantially spherically shaped microspheres. The microspheres may then be dried to a desired residual moisture content and sized by sieving.

In other embodiments, the pore creating material may comprise a liposome. Generally, liposomes comprise an enclosed lipid droplet having a core, typically an aqueous core, containing a compound, such as a therapeutic agent. The therapeutic agent may be chemically conjugated to a lipid component of the liposome. Alternatively, the therapeutic agent may be simply contained within the aqueous compartment inside the liposome or, for hydrophobic therapeutic agents, within the lipid layer of the liposome. Liposomes are commercially available from a variety of suppliers or may be prepared according to known methods, such as the methods described, for example, in U.S. Pat. Nos. 6,855,296 and 6,984,397. In preferred embodiments, liposomes are shaped as microspheres with a diameter between about 50 microns to 400 microns, between about 100 microns to about 300 microns, or between about 100 microns to about 200 microns.

In an exemplary embodiment, the polymer is polymerized or cross-linked without using irradiation, light or heat, in addition, the composition may exclude doxycycline, thrombin, fibrinogen, collagen, gelatin and/or a polysaccharide, and/or have the therapeutic agent substantially absent from the polymer and contained entirely in the pore creating material, and/or completely lacking a fabric support.

In an exemplary embodiment, the polymer comprises poly vinyl alcohol (PVA) and copolymers thereof. In another exemplary embodiment, the polymer is cross-linked using free radical polymerization that is redox initiated.

The invention also relates to the manufacture of a medicament for improving the dynamic stability of an interbody device. The invention also relates to a kit comprising a first container comprising a polymer and a second a container comprising a cross-linking agent, wherein combining the contents of the first container with the contents of the second container initiates polymerization or cross-linking to cure the polymer and retain the interbody device within the subject. Optionally, the kit may contain a third container comprising a therapeutic agent.

For the purposes of the instant disclosure, the term "therapeutic agent" means an agent that promotes, induces, increases, or accelerates wound healing or initiates, accelerates or improves tissue growth, decreases or prevents growth of undesirable bacteria or fungi, reduces or eliminates the sensation of pain in the patient and/or other agents that provide a beneficial effect to a patient or subject. Suitable therapeutic agents include, but are not limited to, antibiotics such as tetracyclines (e.g., minocycline), rifamycins (e.g., rifampin), macrolides (e.g., erythromycin), penicillins (e.g., nafcillin), cephalosporins (e.g., cefazolin), other beta-lactam antibiotics (e.g., imipenem, aztreonam), aminoglycosides (e.g., gentamicin), chloramphenicol, sufonamides (e.g., sulfamethoxazole), glycopeptides (e.g., vancomycin), quinolones (e.g., ciprofloxacin), fusidic acid, trimethoprim, metronidazole, clindamycin, mupirocin, polyenes (e.g., amphotericin B), azoles (e.g., fluconazole) and beta-lactam inhibitors (e.g., sulbactam); analgesics such as acetaminophen, aspirin, clonidine, flurbiprofen, indoprofen, naproxol, pentazocine, proxazole, tramadol, verilopam, volazocine, xylazine, zucapsaicin, phenyhydantoin, phenobarbital, primidone, carbamazepine, ethosuximide, methsuximide, phensuximide, trimethadione, diazepam, benzodiazepines, phenacemide, pheneturide, acetazolamide, sulthiame, morphine, heroin, hydromorphone, metopon, oxymorphone, levorphanol, codeine, hydrocodone, oxycodone, nalorphine, naloxone, naltrexone, salycilates, phenylbutazone, indomethacin, and phenacetin; anti-cytokines; cytokines; anti-interleukin-1 components (anti-IL-1); anti-TNF alpha; stem cells, including autogenic or allogeninc mesenchymal stem cells, bone marrow aspirate, and/or adipose tissue-derived stromal cells; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3;. Fibroblast Growth Factors (FGFs); Platelet Derived Growth Factors (PDGFs), including PDGF-A, PDGF-B, PDGF-C, and PDGF-D; Growth Differentiation Factors, including rhGDF-5; insulin-related growth factor-I (IGF-I); insulin-related growth factor-II (IGF-II); fibroblast growth factor (FGF); beta-2-microglobulin (BDGF II); Bone Morphogenetic Proteins (BMPs), including BMP-2, BMP-7 and BMP-12; Transforming Growth Factor betas (TGF-βs), including TGF-β-1, TGF-β-2, and TGF-β-3; Nell-1 protein; LIM mineralization protein and peptides (see U.S. Patent Publication 2005/0196387); matrix metalloproteinases (MMP) inhibitors; and combinations thereof. For example, the polymer may include microspheres containing rifampin, erythromycin, and BMP-2.

Exemplary MMP inhibitors include, but are not limited to, TIMP-1 and TIMP-2. Certain MMP inhibitors are also described in U.S. Patent Publication 2004/0228853.

The therapeutic agent may be incorporated into the pore creating material, and it may be released from the pore creating material as the pore creating material is being removed and/or by diffusion. The therapeutic agent is preferably administered over a period of up to six weeks, between about twenty four hours and about twelve weeks, between about five days and about four weeks, and between about two weeks and about sixteen weeks.

The instant compositions may also include optional physiologically acceptable carriers, excipients or stabilizers, in the form of lyophilized formulations or aqueous solutions. Methods for preparing therapeutic formulations are known and are disclosed, for example, in Remington: The Science and Practice of Pharmacy, 21st edition, Lippincott Williams & Wilkins (2005).

The term "therapeutically effective amount" means a quantity of a therapeutic agent which, when administered to a patient or subject, is sufficient to result in an improvement in subject's condition. The improvement may be determined in a variety of ways. Additionally, the improvement does not mean a cure and may include only a marginal change in the subject's condition.

While the invention has been described in detail in the foregoing description, the same is to be considered as illustrative and not restrictive in character, it being understood that only the preferred embodiment has been shown and described and that all changes and modifications that come within the spirit of the invention are desired to be protected. In addition, all publications, including Patents and Patent Applications, cited herein are hereby incorporated by reference in their entirety.

What is claimed is:

1. A method of improving retention of an interbody device within a subject, the method comprising:
    creating an opening in at least a portion of an annulus of a disc in a subject;
    inserting an interbody device through the opening in at least a portion of the annulus, wherein the interbody device has at least one hollow space within the interbody device;
    injecting a biologically compatible polymer and a cross-linking agent into the opening in at least a portion of the annulus, wherein the biologically compatible polymer fills a space around the interbody device and through the hollow space within the interbody device to promote tissue growth around and through the interbody device;
    curing the biologically compatible polymer within the opening in at least a portion of the annulus;
    sealing the opening in at least a portion of the annulus to retain the interbody device within the subject;
    delivering a composition comprising a bioabsorbable liposome as a pore creating material and the biologically compatible polymer, wherein the liposome comprises an enclosed liquid droplet having an aqueous core, and further wherein the pore creating material has a rate of removal from the subject's body that is faster than a rate of removal of the biologically compatible polymer from the subject's body;
    incorporating a therapeutic agent within the pore creating material, the therapeutic agent chemically conjugated to a lipid component of the liposome or otherwise contained within said aqueous core of the liposome; and
    removing the pore creating material from the biologically compatible polymer in vivo after the composition is delivered to the subject, wherein the therapeutic agent is released as the pore creating material is being removed.

2. The method according to claim 1, wherein the therapeutic agent is BMP-2.

3. The method according to claim 1, wherein the therapeutic agent is an antimicrobial agent or an analgesic.

4. The method according to claim 1, wherein the biologically compatible polymer comprises poly vinyl alcohol (PVA) and copolymers thereof.

5. The method according to claim 1, wherein inserting an interbody device through the opening in at least a portion of the annulus comprises inserting an interbody device comprising two articulating members.

6. The method according to claim 5, further comprising injecting the biologically compatible polymer and the cross-linking agent into the opening in at least a portion of the annulus and between the two articulating members.

7. The method according to claim 6, wherein the cured biologically compatible polymer forms a resilient structure between the two articulating members of the interbody device.

8. A method of improving dynamic stability of an interbody device, the method comprising:
    inserting an interbody device having at least two articulating members into a subject;
    applying a biologically compatible polymer and a cross-linking agent between the two articulating members of the interbody device, wherein the biologically compatible polymer fills a space around the articulating members and between the articulating members of the interbody device to promote tissue growth around and between the articulating members;
    curing the biologically compatible polymer in situ to form a resilient structure between the two articulating members of the interbody device, and thereby improving dynamic stability of the interbody device;
    delivering a composition comprising a bioabsorbable liposome as a pore creating material and the biologically compatible polymer, wherein the composition excludes collagen, further wherein the liposome comprises an enclosed liquid droplet having an aqueous core, and further wherein the pore creating material has a rate of removal from the subject's body that is faster than a rate of removal of the biologically compatible polymer from the subject's body;
    incorporating a therapeutic agent within the pore creating material, the therapeutic agent chemically conjugated to a lipid component of the liposome or otherwise contained within said aqueous core of the liposome, wherein the therapeutic agent is contained in the pore creating material; and removing the pore creating material from the biologically compatible polymer in vivo after the composition is delivered to the subject, wherein the therapeutic agent is released as the pore creating material is being removed, wherein the biologically compatible polymer is absorbed or degraded in the subject over a period of 3 months to 9 months and the therapeutic agent is released in the subject over a period of between 24 hours and 12 weeks.

9. A method of improving retention of an interbody device within a subject, the method comprising:

inserting an interbody device having at least one hollow space, opening or indentation into a subject;

applying a biologically compatible, hydrophilic polymer and a cross-linking agent into the at least one hollow space, opening or indentation of the interbody device, wherein the biologically compatible polymer fills a space around the interbody device and through the at least one hollow space, opening, or indentation within the interbody device to promote tissue growth around and through the interbody device;

curing the biologically compatible, hydrophilic polymer in situ within the at least one hollow space, opening or indentation of the interbody device, thereby improving retention of the interbody device within the subject;

delivering a composition comprising a bioabsorbable liposome as a pore creating material and the biologically compatible, hydrophilic polymer, wherein the liposome comprises an enclosed liquid droplet having an aqueous core, and further wherein the pore creating material has a rate of removal from the subject's body that is faster than a rate of removal of the biologically compatible, hydrophilic polymer from the subject's body; and incorporating a therapeutic agent within the pore creating material, the therapeutic agent chemically conjugated to a lipid component of the liposome or otherwise contained within said aqueous core of the liposome, wherein the therapeutic agent is contained in the pore creating material;

removing the pore creating material from the biologically compatible, hydrophilic polymer in vivo after the composition is delivered to the subject, wherein the therapeutic agent is released as the pore creating material is being removed, wherein the biologically compatible, hydrophilic polymer is absorbed or degraded in the subject over a period of 3 months to 9 months and the therapeutic agent is released in the subject over a period of between 24 hours and 12 weeks.

10. The method according to claim 9, wherein the pore creating material comprises microspheres.

11. The method according to claim 10, wherein the microspheres are made from hydrogel, fast resorbing cements, ceramics, hyaluronic acid, sugars, polysaccharides, chitin, or combinations thereof.

12. The method according to claim 9, wherein the therapeutic agent is BMP-2.

13. The method according to claim 9, wherein the biologically compatible, hydrophilic polymer comprises poly vinyl alcohol (PVA) and copolymers thereof and the biologically compatible, hydrophilic polymer is polymerized or cross-linked without using irradiation, light or heat.

14. The method according to claim 9, further comprising the subject absorbing the pore creating material within about two weeks.

15. The method according to claim 14, further comprising creating a porosity in the biologically compatible, hydrophilic polymer of about 20 percent to about 60 percent.

16. The method according to claim 14, wherein the therapeutic agent is selected from a group consisting of PDGF, IGF, TGF-Beta, BMPs and combinations thereof.

17. The method according to claim 9, wherein the composition excludes at least one of doxycycline, thrombin, fibrinogen, collagen, gelatin and a polysaccharide; and further wherein the therapeutic agent is an analgesic, an anti-microbial agent, or a bone growth agent.

* * * * *